(12) United States Patent
Mews et al.

(10) Patent No.: US 8,241,347 B2
(45) Date of Patent: Aug. 14, 2012

(54) MEDICAL SUPPORTING IMPLANT, IN PARTICULAR STENT

(75) Inventors: Steffen Mews, Rostock (DE); Frank Bakczewitz, Rostock (DE)

(73) Assignee: Biotronik VI Patent AG, Baar (CH)

( * ) Notice: Subject to any disclaimer, the term of this patent is extended or adjusted under 35 U.S.C. 154(b) by 424 days.

(21) Appl. No.: 12/412,417

(22) Filed: Mar. 27, 2009

(65) Prior Publication Data

US 2009/0248136 A1 Oct. 1, 2009

(30) Foreign Application Priority Data

Mar. 29, 2008 (DE) .......................... 10 2008 016 363

(51) Int. Cl.
*A61F 2/82* (2006.01)
(52) U.S. Cl. ..................................... 623/1.15
(58) Field of Classification Search ................ 623/1.15, 623/1.17, 23.7
See application file for complete search history.

(56) References Cited

U.S. PATENT DOCUMENTS

| 5,441,515 A | 8/1995 | Khosravi et al. |
| 5,797,951 A | 8/1998 | Mueller |
| 5,824,054 A | 10/1998 | Khosravi et al. |
| 2002/0042648 A1* | 4/2002 | Schaldach et al. ........... 623/1.15 |
| 2003/0004563 A1 | 1/2003 | Jackson et al. |
| 2006/0030931 A1* | 2/2006 | Shanley ....................... 623/1.15 |
| 2007/0061004 A1 | 3/2007 | Steinke et al. |

FOREIGN PATENT DOCUMENTS

| DE | 19728337 A1 | 1/1999 |
| DE | 102004003093 A1 | 8/2005 |
| WO | 9940874 A1 | 8/1999 |
| WO | 2006107608 A1 | 10/2006 |
| WO | 2007016409 A1 | 2/2007 |

OTHER PUBLICATIONS

Search Report for European Patent Application No. 09154203.5; Apr. 22, 2009.
Search Report for German Patent Application No. 10 2008 016 363.5; Jan. 12, 2009.

* cited by examiner

*Primary Examiner* — Ryan Severson
(74) *Attorney, Agent, or Firm* — Greer, Burns & Crain, Ltd.

(57) ABSTRACT

A medical supporting implant, in particular a stent, comprises a tubular base body which is made up of bendable struts (2), such that at node points (4) of at least two struts (2), the bendable struts (2) form an acute angle (W) to one another which angle becomes larger on dilatation of the implant with plastic deformation of the struts (2) at the node point (4). At least a portion of the struts (2) between the plastic deformation areas (4) is provided with a telescoping ratchet mechanism (R) for irreversible lengthening of the respective struts (2) on dilatation.

8 Claims, 4 Drawing Sheets

US 8,241,347 B2

MEDICAL SUPPORTING IMPLANT, IN PARTICULAR STENT

PRIORITY CLAIM

This patent application claims priority to German Patent Application No. 10 2008 016 363.5, filed Mar. 29, 2008, the disclosure of which is incorporated herein by reference in its entirety.

FIELD

The present disclosure relates to a medical implant, in particular, a stent.

BACKGROUND

Such medical supporting implants are used primarily for treatment of stenoses in coronary vessels, but may also be used for other indications in other types of vessels in the body. As a rule, such supporting implants have a tubular base body comprising flexible struts formed from the base body by laser cutting. A wide variety of designs are known for the strut structure. The starting point for the present disclosure is stent designs with meandering peripheral supporting struts such that, at node points of at least two struts, the struts form an acute angle with one another. On dilatation of the implant, this acute angle increases under bending stress on the struts at the node. One problem with such stents is that during crimping the stent is compressed into the state for inserting the stent into the respective vessel on a balloon catheter, and a great plastic deformation then occurs which has a significant influence on the elastic recoil of the stent structure. The goal is for the recoil effect to be minimized. This can be ensured to a limited extent by local plastic deformation of the stent structure, e.g., in the area of the node points between neighboring struts of the peripheral supporting webs. However, due to the material, there are limits to the plastic deformation. When these limits are exceeded, there is the risk of a structural failure, e.g., on reaching the elongation at break in the material.

Due to the restriction that material-specific limit values must not be exceeded, it is problematical accordingly to achieve good recoil performance with the stent. Enlarging the cross section of the struts of the stent structure is also possible only to a limited extent.

To solve the above problems, approaches for making stent structures expandable through mechanical constructions without plastic deformation are already known. U.S. Pat. No. 5,824,054 discloses a vascular supporting implant comprising a polytetrafluoroethylene ("PTFE") film sheet with peripheral rows of perforations coiled onto itself. Projections integrally molded on the foam sheet may mesh with the perforations, these projections being aligned so that compression of the stent is prevented.

U.S. Pat. No. 5,441,515 discloses a "ratchet stent," as it is referred to therein, in which the cylindrical stent structure is formed by tongues running circumferentially. These tongues are held together by a common connecting crosspiece, a slot for engagement of the end of the tongue being arranged in each crosspiece. On their lateral edges, the tongues are provided with rows of locking teeth which act unidirectionally. The tongue ends are inserted far into the slots in the compressed position. When the stent is dilated, the tongues gradually expand outward out of the slots preventing contraction by the locking teeth engaging with the slot ends.

Finally, U.S. Patent Publication No. 2007/0061004 discloses an expanded stent in which mesh structures running in the circumferential direction are subdivided into individual sections which allow widening of the stent structure by displacement of the individual elements toward one another. The mesh structures with strap-like protrusions engage in corresponding openings in the neighboring mesh structure.

SUMMARY

The present disclosure describes several exemplary embodiments of the present invention.

One aspect of the present disclosure provides a medical supporting implant, such as a stent, comprising: a tubular base body comprising a plurality of bendable struts having node points, whereby at the node points of at least two struts, the struts are at an acute angle to one another, wherein the angle becomes larger on dilatation of the implant with plastic deformation areas of the struts at the node point, and wherein at least a portion of the struts between the plastic deformation areas includes a telescoping ratchet mechanism for irreversible lengthening of the respective struts in dilatation.

Another aspect of the present disclosure provides a stent designed for supporting implants in which a larger widening area from the crimpled state can be achieved with only limited deformation of the plastic deformation areas.

The present disclosure provides a telescoping ratchet mechanism for at least some of the struts between the plastic deformation areas for irreversible lengthening of the respective strut when the stent is dilated.

The supporting implant thus follows in its basic structure the conventional balloon-expandable design comprising meandering circumferential supporting webs which undergo plastic deformation between two neighboring struts at the node points when dilated. In addition, in their undeformed straight passages between their plastic deformation areas, the meandering supporting webs are provided with a ratchet mechanism which is preferably formed by two strut arms flanking one another, displaceable toward one another in the longitudinal direction by locking teeth acting unidirectionally but being blocked in the opposite direction. Through the relative movement of the strut arms involved, an increase in diameter significantly beyond plastic deformation can be achieved. In doing so, the flanking strut arms are prevented from slipping back and thus recoil of the entire structure is prevented by interlocking of the webs. The dilatation path thus comprises firstly the plastic deformation of the meandering loops and secondly the telescoping movement of the extendable struts in the circumferential direction. Since elastic recoil originates only from the deformation of the webs themselves, the recoil is reduced on the whole.

BRIEF DESCRIPTION OF THE DRAWINGS

Various aspects of the present disclosure are described hereinbelow with reference to the accompanying figures.

Additional features, details and advantages of the invention are derived from the following description, which explains in greater detail an exemplary embodiment on the basis of the accompanying drawings.

DETAILED DESCRIPTION

Figure 1:
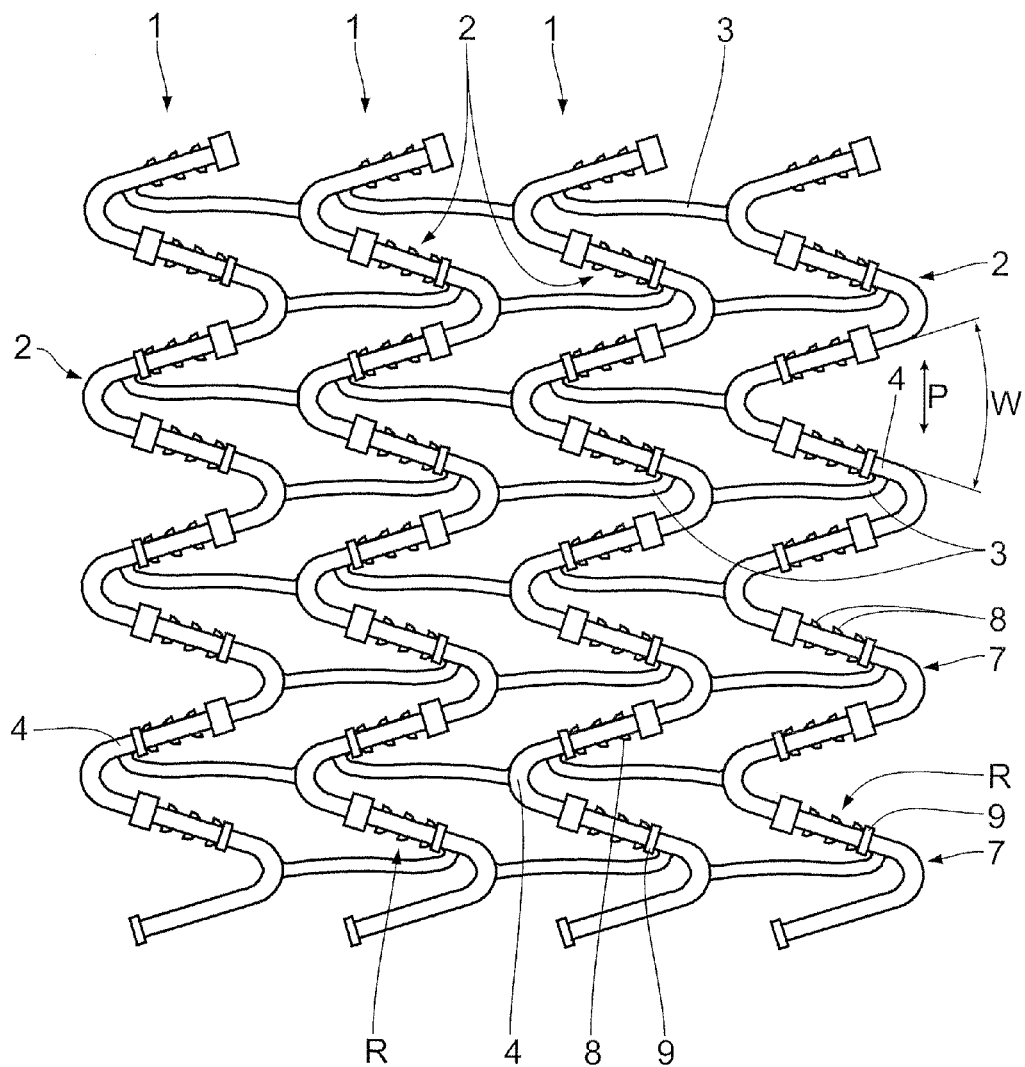
FIG. 1 shows an enlarged detailed view of a stent structure according to one exemplary embodiment of the present invention in the crimped state in the developed diagram of FIG. 2.
Figure 2:
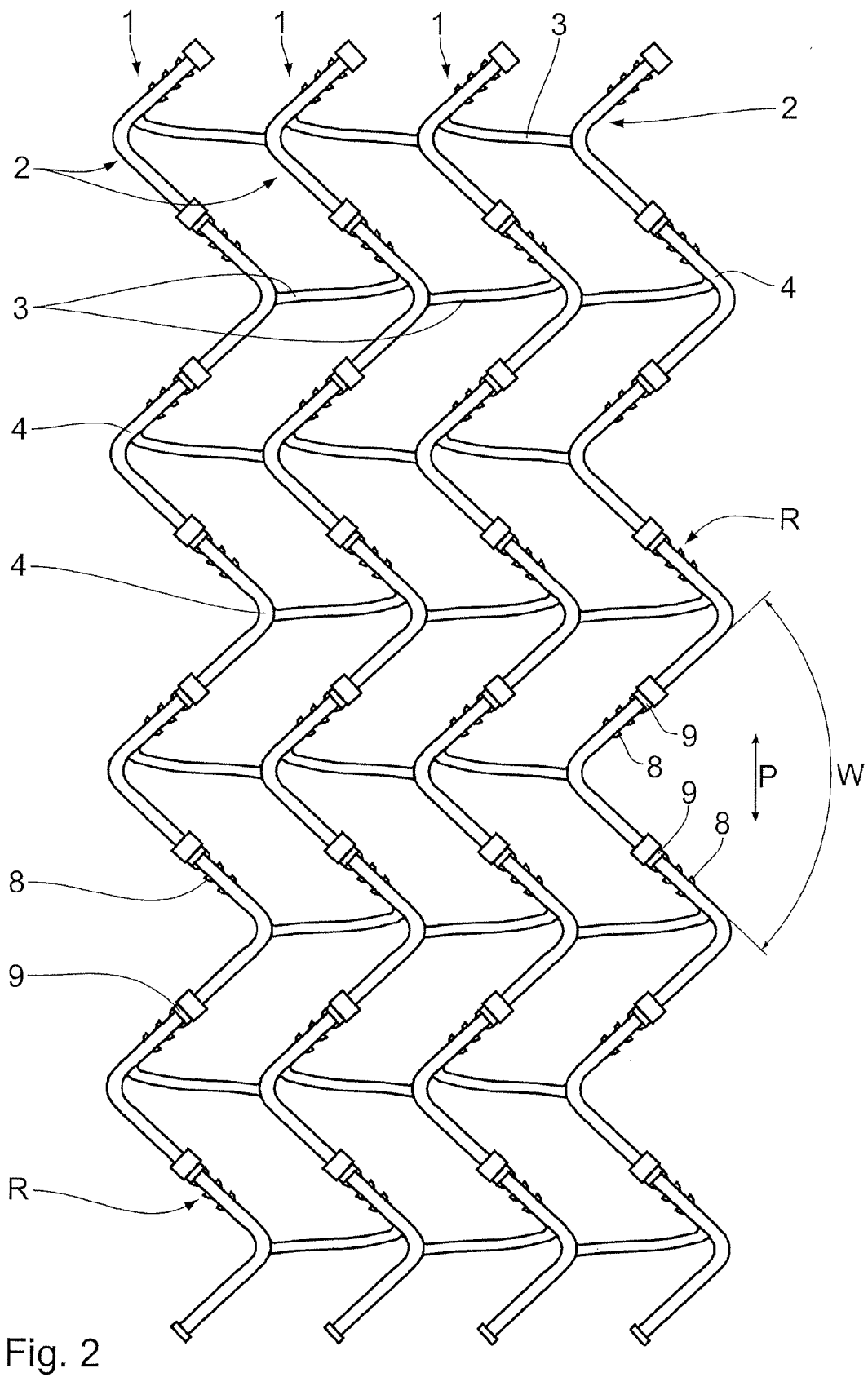
FIG. 2 shows a detailed view of the stent structure shown in FIG. 1 in a dilated state.

As FIGS. 1 and 2 show clearly in one exemplary embodiment of the present disclosure, the stent structure consists of circumferential meandering supporting webs 1 which run in the peripheral direction P and are made of struts 2 connected to one another at an acute angle W. Parallel to the longitudinal direction of the stent 1, the individual supporting webs are linked together by axial connectors 3. On the whole, a basic tubular structure (not shown) is formed from the stent structure shown in FIG. 1 and can be dilated from a crimped contracted basic position into a supporting position in a vessel by radial expansion, e.g., with the help of a balloon. In the dilatation process, the node points 4 between two neighboring struts 2 are expanded and undergo plastic deformation accordingly. The angle W therefore increases under bending stress on the struts 2 at the respective node point 4, as illustrated in FIG. 2.

Figure 3:
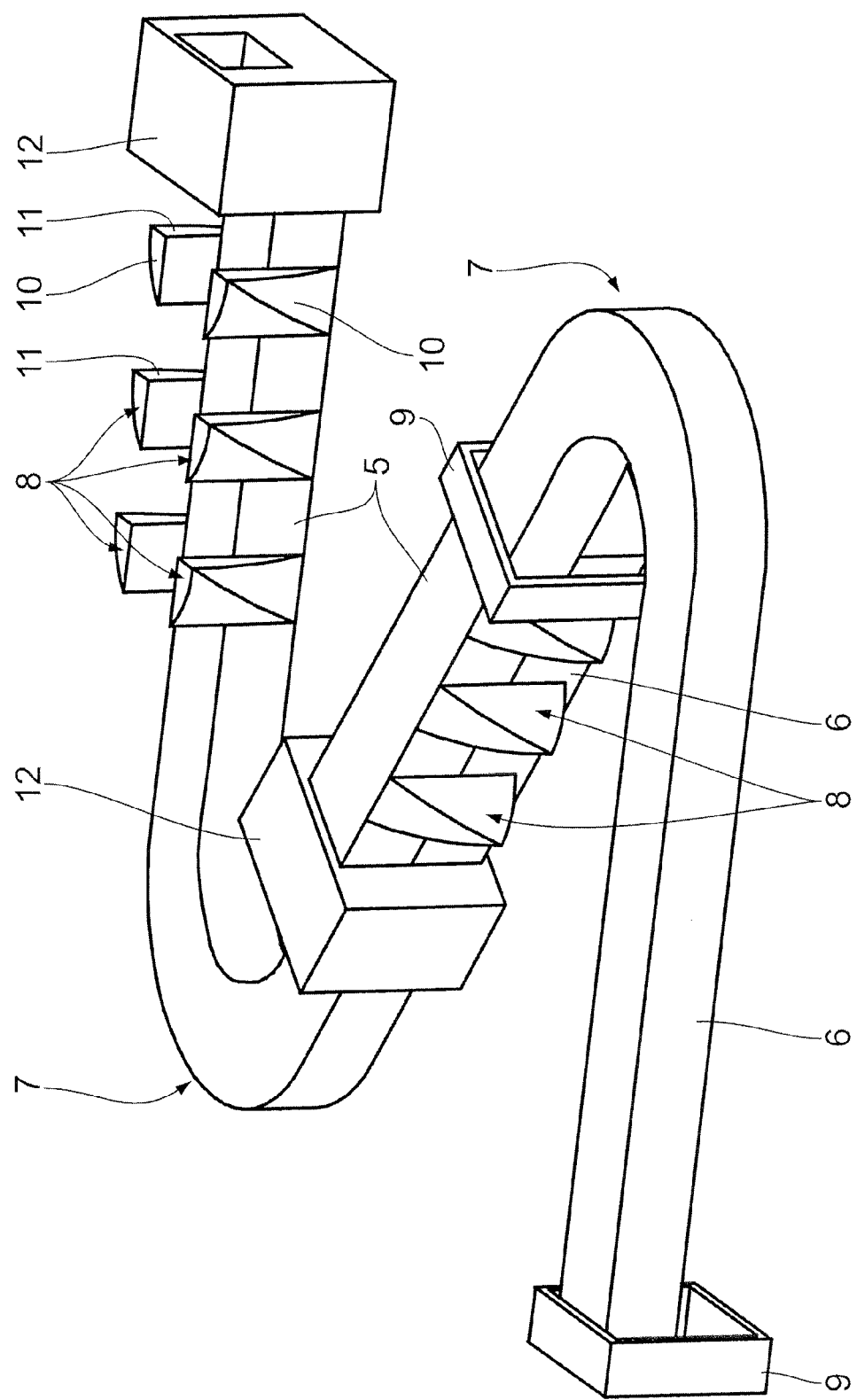
FIG. 3 shows a perspective diagram of a strut section in an undilated starting state.
Figure 4:
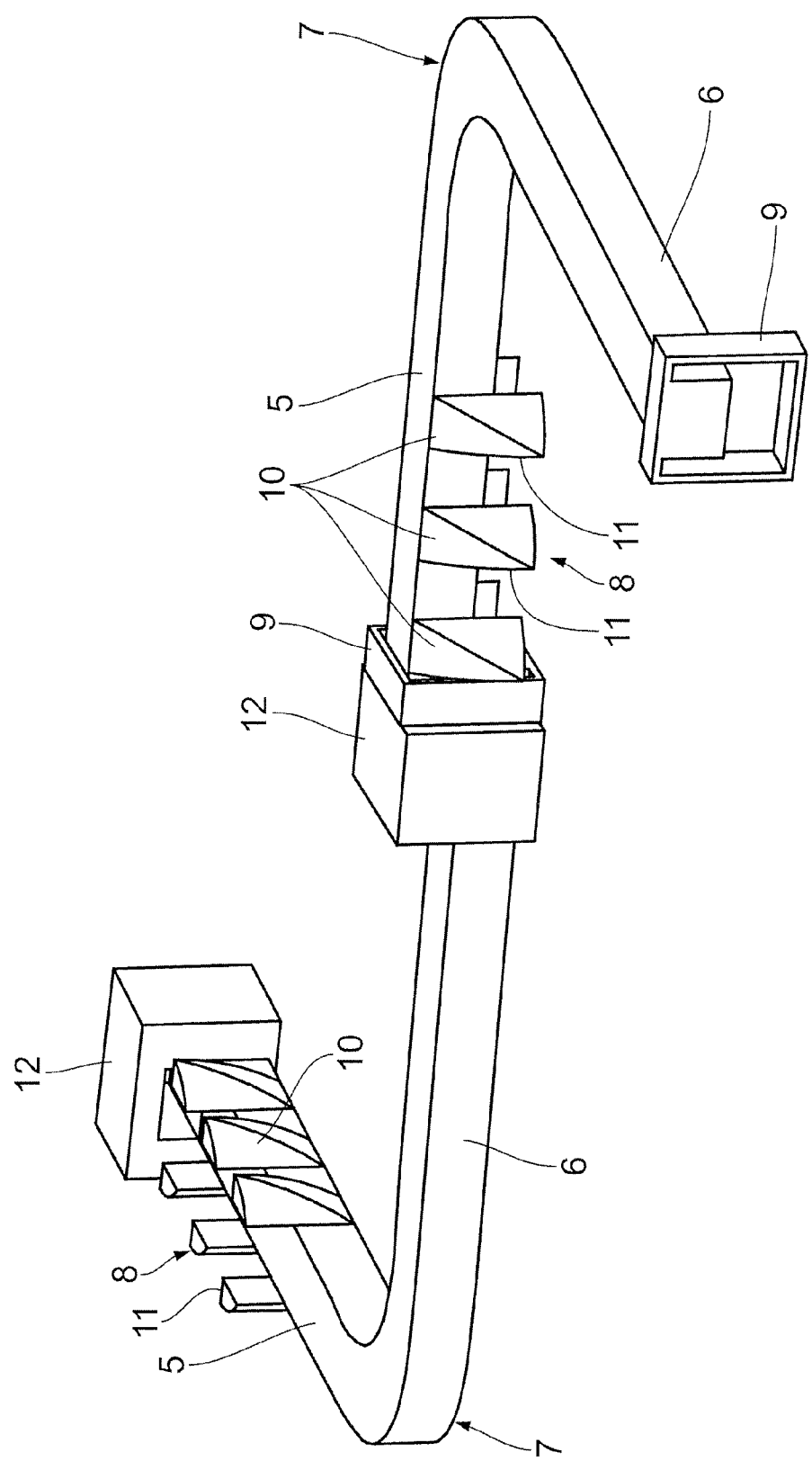
FIG. 4 shows a perspective view of the strut section from another direction of view in a dilated state.

The struts 2 are each formed by two flanking strut arms 5, 6, as shown clearly in FIGS. 3 and 4. Each supporting web 1 is thus composed of approximately V-shaped strut components 7 whose legs form the strut arms 5, 6. Locking teeth 8 acting unidirectionally are integrally molded on the sides of the strut arms 5 forming a ratchet mechanism R together with a frame-shaped locking sleeve 9 arranged across the longitudinal direction of the arm on the free end of the other strut arm 6. With the help of this locking mechanism, each strut 2 can be irreversibly lengthened on dilatation. As is clear from FIG. 3 in combination with FIG. 1, in the contracted starting position of the stent, the two strut arms 5, 6 of one strut are each pushed together at least to form a large longitudinal part thus yielding a short length of the strut 2. In dilatation of the stent, the two strut arms 5, 6 are pulled apart by the corresponding tensile stress so that the locking teeth 8 can be snapped beneath the locking sleeve 9 successively with their sliding flanks 10. Because of the steep locking flank 11 of each locking tooth 8, the two strut arms 5, 6 are then secured in the vessel to prevent the strut arms 5,6 from being pushed together after dilatation because of the radial load on the stent.

As is shown in FIGS. 3 and 4, the sliding flank 10 of the locking teeth 8 is designed to be rounded in two orthogonal planes, namely in the longitudinal direction of the strut arm 5 and across the strut arm 5, so that the locking sleeves 9 can slide over it somewhat more easily.

The strut arms 5 with the locking teeth 8 are also provided with a block-like stop 12 on the free end cooperating with the locking sleeve 9 of the other strut arm 6. The longitudinal limitation on the relative telescoping displacement of the two strut arms 5, 6 prevents the connection between the two arms 5, 6 from being released, as shown in FIG. 4.

On the whole, the ratchet mechanism R can be compared with a cable tie locking mechanism. Generally speaking, the stent has a recoil behavior due only to the plastic deformation of the struts 2, which turns out to be less than the recoil behavior of comparable stent structures not having this ratchet mechanism R due to the lengthening of the struts 2, which is achieved with the help of the telescoping ratchet mechanism R and the associated increase in diameter of the stent without any increase in bending stress.

All patents, patent applications and publications referred to herein are incorporated by reference in their entirety.

What is claimed is:

1. A medical supporting implant, such as a stent, comprising: a tubular base body comprising a plurality of bendable struts having node points, whereby at the node points of at least two struts, the struts are at an acute angle to one another, wherein the angle becomes larger on dilatation of the implant with plastic deformation areas of the struts at the node point, and wherein at least a portion of the struts between the plastic deformation areas includes a telescoping ratchet mechanism for irreversible lengthening of the respective struts in dilatation.

2. The medical supporting implant of claim 1, wherein the ratchet mechanism comprises two flanking strut arms which are displaceable toward one another in the longitudinal direction but are blocked in the opposite direction by a plurality of locking teeth that act unidirectionally.

3. The medical supporting implant of claim 2, wherein the plurality of locking teeth are arranged so the teeth are aligned in rows on one strut arm.

4. The medical supporting implant of claim 2, wherein the locking teeth of a strut arm engage with a locking sleeve on the flanking strut arm.

5. The medical supporting implant of claim 2, wherein each of the locking teeth further comprises a rigid locking flank portion and a sliding flank portion.

6. The medical supporting implant of claim 5, wherein the sliding flank portion of each of the locking teeth has a portion which is rounded in two essentially orthogonal planes.

7. The medical supporting implant of claim 2, wherein the strut arm having the locking teeth has a stop on the end thereof for limiting the length of the relative telescoping movement of the strut arms.

8. A medical supporting implant, such as a stent, comprising: a tubular base body comprising a plurality web segments, with adjacent web segments being connected by a plurality of elongated axial connectors, each web segment having a plurality of connected bendable generally V-shaped struts, each strut including a node point being formed by an adjacent first strut arm and second strut arm, each strut arm having a top, bottom, left and right side, the adjacent first and second strut arms forming an acute angle with respect to one another, wherein the angle becomes larger upon dilatation of the base body, each node point having a portion defining a plastic deformation area, a set of locking teeth extending from at least one side of one strut arm of each strut, and a locking sleeve associated with the first strut arm, and a telescoping ratchet mechanism formed by a first plastic deformation area and a second plastic deformation area, a first locking sleeve associated with a second strut arm of a first plastic deformation area, and a second locking sleeve associated with a first strut arm of a second plastic deformation area such that the locking teeth are adapted to engage the second locking sleeve, wherein when the base body is in a non-dilated configuration the first plastic deformation area first strut arm and locking teeth at least partially overlap the second plastic deformation area second strut arm and wherein the first plastic deformation area first strut arm bottom surface is proximate to the second plastic deformation area second strut arm top surface, and wherein when the base body is in a dilated configuration the first plastic deformation area first strut arm and locking teeth slidingly move to engage the second plastic deformation area second locking sleeve so as to irreversibly lengthen the distance between adjacent first and second plastic deformation areas.

* * * * *